US008491596B2

(12) United States Patent
Long et al.

(10) Patent No.: US 8,491,596 B2
(45) Date of Patent: Jul. 23, 2013

(54) METHOD FOR REMOVAL OF BONE

(75) Inventors: Jack Long, Warsaw, IN (US); Brian Maroney, Fort Wayne, IN (US); Jose Guzman, Fort Wayne, IN (US); Frank G. Alvine, Sioux Falls, SD (US); Stephen F. Conti, Pittsburgh, PA (US); Roy W. Sanders, Tampa, FL (US)

(73) Assignee: DePuy Products, Inc., Warsaw, IN (US)

( * ) Notice: Subject to any disclaimer, the term of this patent is extended or adjusted under 35 U.S.C. 154(b) by 423 days.

(21) Appl. No.: 12/400,627

(22) Filed: Mar. 9, 2009

(65) Prior Publication Data
US 2010/0023066 A1 Jan. 28, 2010

Related U.S. Application Data

(63) Continuation of application No. 10/177,966, filed on Jun. 21, 2002, now abandoned.

(51) Int. Cl.
*A61B 17/58* (2006.01)
*A61B 17/60* (2006.01)
*A61F 2/00* (2006.01)

(52) U.S. Cl.
USPC .......................................................... 606/96

(58) Field of Classification Search
USPC ....... 606/53, 79–80, 86 R–89, 96; 623/21.18, 623/20.33, 23.39, 47–48
See application file for complete search history.

(56) References Cited

U.S. PATENT DOCUMENTS

| 1,630,239 | A | | 5/1927 | Binkley et al. |
|---|---|---|---|---|
| 1,723,517 | A | | 8/1929 | McFadden |
| 3,820,167 | A | | 6/1974 | Sivash |
| 3,835,858 | A | | 9/1974 | Hagen |
| 3,839,742 | A | | 10/1974 | Link |
| 3,855,638 | A | | 12/1974 | Pilliar |
| 3,867,932 | A | | 2/1975 | Huene |
| 3,872,519 | A | * | 3/1975 | Giannestras et al. ...... 623/21.18 |
| 3,886,599 | A | | 6/1975 | Schlein |
| 3,889,300 | A | | 6/1975 | Smith |
| 3,896,502 | A | | 7/1975 | Lennox |
| 3,943,576 | A | | 3/1976 | Sivash |
| 3,975,778 | A | | 8/1976 | Newton, III |

(Continued)

FOREIGN PATENT DOCUMENTS

| DE | 19501550 | 7/1996 |
|---|---|---|
| EP | 0327249 A2 | 8/1989 |

(Continued)

OTHER PUBLICATIONS

ADVANCE Unicompartmental Knee System Surgical Technique—Wright Medical Technology (12 pages).

(Continued)

*Primary Examiner* — William H. Matthews
(74) *Attorney, Agent, or Firm* — Maginot, Moore & Beck, LLP

(57) ABSTRACT

A kit (10) for preparation of a bone cavity (12) in a bone (14) for implantation of a joint prosthesis (16) is provided. The kit (10) includes a guide (20) defining an opening (22) therethrough. The guide (20) is in cooperation with the prosthesis. The kit (10) also includes a rotatable tool (24) constrainable within the opening (22) of said guide (20). The tool (24) is adapted for removal of bone (14) to form the bone cavity (12).

22 Claims, 20 Drawing Sheets

U.S. PATENT DOCUMENTS

| | | | |
|---|---|---|---|
| 3,987,500 A | 10/1976 | Schlein | |
| 3,996,625 A | 12/1976 | Noiles | |
| 4,021,864 A | 5/1977 | Waugh | |
| 4,069,518 A | 1/1978 | Groth, Jr. et al. | |
| 4,077,070 A | 3/1978 | Sivash | |
| 4,232,404 A | 11/1980 | Samuelson et al. | |
| 4,421,112 A | 12/1983 | Mains et al. | |
| 4,450,591 A | 5/1984 | Rappaport | |
| 4,467,801 A | 8/1984 | Whiteside | |
| 4,470,158 A | 9/1984 | Pappas et al. | |
| 4,474,177 A | 10/1984 | Whiteside | |
| 4,524,766 A | 6/1985 | Petersen | |
| 4,530,114 A | 7/1985 | Tepic | |
| 4,551,863 A | 11/1985 | Murray | |
| 4,567,885 A | 2/1986 | Androphy | |
| 4,703,751 A | 11/1987 | Pohl | |
| 4,708,139 A | 11/1987 | Dunbar, IV | |
| 4,719,908 A | 1/1988 | Averill et al. | |
| 4,721,104 A * | 1/1988 | Kaufman et al. | 606/88 |
| 4,755,185 A | 7/1988 | Tarr | |
| 4,784,126 A | 11/1988 | Hourahane | |
| 4,790,852 A | 12/1988 | Noiles | |
| 4,846,839 A | 7/1989 | Noiles | |
| 4,865,603 A | 9/1989 | Noiles | |
| 4,885,603 A | 12/1989 | Tomizawa et al. | |
| 4,892,093 A | 1/1990 | Zarnowski et al. | |
| 4,926,847 A | 5/1990 | Luckman | |
| 4,952,213 A | 8/1990 | Bowman et al. | |
| 4,952,214 A | 8/1990 | Comparetto | |
| 4,968,316 A | 11/1990 | Hergenroeder | |
| 5,011,496 A | 4/1991 | Forte et al. | |
| 5,035,699 A * | 7/1991 | Coates | 606/86 R |
| 5,053,037 A | 10/1991 | Lackey | |
| 5,122,144 A | 6/1992 | Bert et al. | |
| 5,147,364 A | 9/1992 | Comparetto | |
| 5,163,940 A | 11/1992 | Bourque | |
| 5,167,619 A | 12/1992 | Wuchinich | |
| 5,190,547 A | 3/1993 | Barber, Jr. et al. | |
| 5,207,712 A | 5/1993 | Cohen | |
| 5,234,433 A | 8/1993 | Bert et al. | |
| 5,246,444 A | 9/1993 | Schreiber | |
| 5,257,995 A | 11/1993 | Umber et al. | |
| 5,282,803 A | 2/1994 | Lackey | |
| 5,290,291 A | 3/1994 | Linden | |
| 5,295,992 A | 3/1994 | Cameron | |
| 5,312,411 A | 5/1994 | Steele et al. | |
| 5,312,412 A | 5/1994 | Whipple | |
| 5,314,482 A | 5/1994 | Goodfellow et al. | |
| 5,326,365 A | 7/1994 | Alvine | |
| 5,342,368 A | 8/1994 | Petersen | |
| 5,344,423 A | 9/1994 | Dietz et al. | |
| 5,360,450 A | 11/1994 | Giannini | |
| 5,364,402 A | 11/1994 | Mumme et al. | |
| 5,395,376 A | 3/1995 | Caspari et al. | |
| 5,403,321 A | 4/1995 | DiMarco | |
| 5,409,489 A | 4/1995 | Sioufi | |
| 5,449,360 A | 9/1995 | Schreiber | |
| 5,454,816 A | 10/1995 | Ashby | |
| 5,474,559 A | 12/1995 | Bertin et al. | |
| 5,484,437 A | 1/1996 | Michelson | |
| 5,484,446 A | 1/1996 | Burke et al. | |
| 5,486,180 A | 1/1996 | Dietz et al. | |
| 5,489,180 A | 2/1996 | Ichihara et al. | |
| 5,496,324 A * | 3/1996 | Barnes | 606/79 |
| 5,520,695 A | 5/1996 | Luckman | |
| 5,534,005 A | 7/1996 | Tokish, Jr. et al. | |
| 5,540,692 A | 7/1996 | Tidwell | |
| 5,562,674 A | 10/1996 | Stalcup et al. | |
| 5,571,110 A | 11/1996 | Matsen, III et al. | |
| 5,584,839 A * | 12/1996 | Gieringer | 606/96 |
| 5,593,411 A | 1/1997 | Stalcup et al. | |
| 5,601,563 A | 2/1997 | Burke et al. | |
| 5,613,970 A | 3/1997 | Houston et al. | |
| 5,613,971 A | 3/1997 | Lower et al. | |
| 5,624,443 A | 4/1997 | Burke | |
| 5,624,444 A | 4/1997 | Wixon et al. | |
| 5,624,463 A | 4/1997 | Stone et al. | |
| 5,634,927 A | 6/1997 | Houston et al. | |
| 5,643,272 A | 7/1997 | Haines et al. | |
| 5,653,714 A | 8/1997 | Dietz et al. | |
| 5,683,397 A | 11/1997 | Vendrely et al. | |
| 5,709,689 A | 1/1998 | Ferrante et al. | |
| 5,733,290 A | 3/1998 | McCue et al. | |
| 5,743,910 A | 4/1998 | Bays et al. | |
| 5,766,259 A | 6/1998 | Sammarco | |
| 5,769,854 A | 6/1998 | Bastian et al. | |
| 5,810,827 A | 9/1998 | Haines et al. | |
| 5,879,354 A | 3/1999 | Haines et al. | |
| 5,902,340 A | 5/1999 | White et al. | |
| 5,916,220 A | 6/1999 | Masini | |
| 5,925,049 A | 7/1999 | Gustilo et al. | |
| 5,938,665 A | 8/1999 | Martin | |
| 6,056,754 A | 5/2000 | Haines et al. | |
| 6,090,114 A | 7/2000 | Matsuno et al. | |
| 6,106,529 A | 8/2000 | Techiera | |
| 6,139,551 A | 10/2000 | Michelson et al. | |
| 6,179,877 B1 | 1/2001 | Burke | |
| 6,183,519 B1 | 2/2001 | Bonnin et al. | |
| 6,187,012 B1 | 2/2001 | Masini | |
| 6,193,723 B1 | 2/2001 | Cripe et al. | |
| 6,197,029 B1 | 3/2001 | Fujimori et al. | |
| 6,197,064 B1 | 3/2001 | Haines et al. | |
| 6,277,121 B1 | 8/2001 | Burkinshaw et al. | |
| 6,321,457 B1 | 11/2001 | Lariviere, Jr. et al. | |
| 6,322,564 B1 | 11/2001 | Surma | |
| 6,342,057 B1 | 1/2002 | Brace et al. | |
| 6,355,045 B1 | 3/2002 | Gundlapalli et al. | |
| 6,361,506 B1 | 3/2002 | Saenger et al. | |
| 6,409,767 B1 | 6/2002 | Pericé et al. | |
| 6,482,209 B1 | 11/2002 | Engh et al. | |
| 6,488,687 B1 | 12/2002 | Masini | |
| 6,520,964 B2 | 2/2003 | Tallarida et al. | |
| 6,537,280 B2 | 3/2003 | Dinger et al. | |
| D473,307 S | 4/2003 | Cooke | |
| 6,554,837 B1 | 4/2003 | Hauri et al. | |
| 6,554,838 B2 | 4/2003 | McGovern et al. | |
| 6,575,980 B1 | 6/2003 | Robie et al. | |
| 6,663,669 B1 | 12/2003 | Reiley | |
| 6,852,130 B2 | 2/2005 | Keller et al. | |
| 6,863,691 B2 | 3/2005 | Short et al. | |
| 6,926,739 B1 | 8/2005 | O'Connor et al. | |
| 7,011,664 B2 | 3/2006 | Haney et al. | |
| 7,033,362 B2 | 4/2006 | McGahan et al. | |
| 7,090,677 B2 | 8/2006 | Fallin et al. | |
| 7,240,588 B1 | 7/2007 | Rinner | |
| 2002/0055744 A1 | 5/2002 | Reiley | |
| 2002/0183760 A1 | 12/2002 | McGovern et al. | |
| 2004/0002768 A1 | 1/2004 | Parks et al. | |
| 2004/0030399 A1 | 2/2004 | Asencio | |
| 2004/0122523 A1 | 6/2004 | Guzman | |
| 2004/0133282 A1 | 7/2004 | Deffenbaugh et al. | |
| 2004/0162619 A1 | 8/2004 | Blaylock et al. | |
| 2004/0167631 A1 | 8/2004 | Luchesi et al. | |
| 2004/0186585 A1 | 9/2004 | Feiwell | |
| 2005/0288792 A1 | 12/2005 | Landes et al. | |
| 2006/0142870 A1 | 6/2006 | Robinson et al. | |
| 2007/0112432 A1 * | 5/2007 | Reiley | 623/21.18 |

FOREIGN PATENT DOCUMENTS

| | | |
|---|---|---|
| EP | 0962190 A2 | 8/1999 |
| EP | 0864304 B1 | 7/2002 |
| EP | 0864305 B1 | 8/2002 |
| EP | 0800803 B1 | 10/2002 |
| EP | 0682916 B1 | 9/2003 |
| FR | 2220235 A1 | 10/1974 |
| FR | 2543821 A3 | 10/1984 |
| FR | 2615726 A1 | 12/1988 |
| FR | 2616059 A1 | 12/1988 |
| FR | 2676917 A1 | 12/1992 |
| FR | 2680968 A1 | 3/1993 |
| FR | 2684291 A1 | 6/1993 |
| FR | 2700462 A1 | 7/1994 |
| FR | 2730157 A1 | 8/1996 |
| FR | 2759900 A1 | 8/1998 |
| FR | 2808994 | 11/2001 |
| WO | 9107931 A1 | 6/1991 |
| WO | 9405211 A1 | 3/1994 |

| | | |
|---|---|---|
| WO | 0067650 | 11/2000 |
| WO | 0067650 A1 | 11/2000 |
| WO | 03034955 A1 | 5/2003 |
| WO | 2005030098 A1 | 4/2005 |
| WO | 2005041823 A1 | 5/2005 |

OTHER PUBLICATIONS

The minimally Invasive Uni Knee System—Stryker Howmedica Osteonics (20 pages).
Australian Examiner's First Report corresponding to Australian Application No. 2003204899, dated Oct. 2, 2007 (3 pages).
Australian Examiner's First Report corresponding to Australian Application No. 2003204786, dated Oct. 2, 2007 (2 pages).
European Examination Report corresponding to European Application No. 03 253 924.9, dated Sep. 27, 2012 (9 pages).
Wright Medical Technology, Advance Unicompartmental Knee System, Surgical Technique, published at least as early as Jun. 20, 2002 (12 pages).
Stryker Howmedica Osteonics, the Minimally Invasive Uni Knee System, Surgical Technique, 2002 (24 pages).
S-ROM Total Hip System Surgical Technique Brochure, 0601-36-050 (Rev. 1), DePuy Orthopaedics, Inc. & DePuy International, Ltd., published in the USA and Leeds England, 2002 (13 pages).
S-ROM Total Hip System Product Codes & Surgical Technique Brochure, DePuy Orthopaedics, Inc., & DePuy International, Ltd., published in the USA and Leeds England, 2002 (8 pages).

* cited by examiner

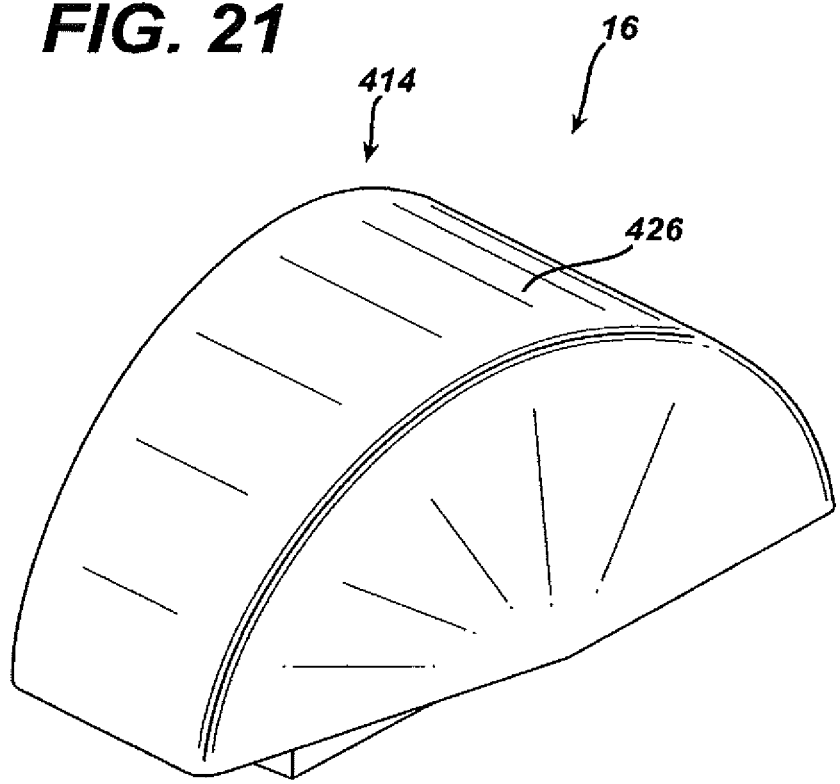

METHOD FOR REMOVAL OF BONE

This application is a continuation of co-pending application Ser. No. 10/177,966, filed on Jun. 21, 2002, the disclosure of which is herein totally incorporated by reference in its entirety.

CROSS-REFERENCE TO RELATED APPLICATIONS

This application is a Continuation of U.S. patent application Ser. No. 10/177,966, filed Jun. 21, 2002 (now abandoned). Cross reference is also made to U.S. application Ser. No. 10/176,934, filed Jun. 21, 2002 and entitled "PROSTHESIS REMOVAL CUTTING GUIDE, CUTTING TOOL AND METHOD" (now U.S. Pat. No. 7,935,118 issued May 3, 2011) and U.S. application Ser. No. 10/176,891, filed Jun. 21, 2002 and entitled "PROSTHESIS CUTTING GUIDE, CUTTING TOOL AND METHOD" (now U.S. Pat. 8,211,113 issued Jul. 3, 2012, the disclosures of which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

Prosthetic devices which are implanted for replacement of joints are well known. Such implants take the place of the body's own joints which fail, such as may be required for patients suffering from rheumatism, degenerative or traumatic arthritis, including osteoarthritis. A number of problems are associated with joint replacement. The joint should function in a manner which simulates the natural joint, providing substantially the same degree of motion.

The ankle joint, or joint between the leg bones, tibia and fibula, and the talus, are frequently a source of osteo or rheumatoid arthritis. Typically, sufferers of rheumatoid and osteoarthritis at the ankle joint have been generally limited to a procedure called fusing. In a fusing procedure, the tibia and talus are fused or secured together to reduce the patient's pain and improve mobility. Clearly, the use of fusing does not provide the same degree of motion as a natural ankle joint.

For example, for ankle replacements, the joint should supply at least the same degree of motion as is required for walking. In addition, the joint should not occupy more space in the body than the natural joint. Problems arise in connection with the replacement joint to bone and tissue. The joint should also be easy to implant as possible so that intricate operations are not required, thus reducing the chance of complications. The joints must have sufficient strength and durability to withstand the weight and stresses which are applied.

Ankle joints pose additional problems due to the weight supported and range of motion required for walking. Attachment of the tibia, which extends substantially vertically is difficult, as portions of the fibula may also be removed for implants. Matching the pivot point of the joint is critical, as misalignment can lead to difficulty in walking and other motions, which may cause the patient considerable pain.

The durability of a replacement joint is also important, as the ankle experiences high stresses during walking, running, and jumping, as well as fatigue over time. These stresses may crack or fracture ankle components of replacement joints, which absorb a substantial amount of the pressures during the aforementioned activities.

A particularly successful ankle implant for use in total ankle arthroplasty is disclosed in U.S. Pat. No. 5,326,365 to Alvine, and assigned to the same assignee as the instant application. U.S. Pat. No. 5,326,365 is hereby incorporated in its entirety by reference.

The total ankle implant, as disclosed in U.S. Pat. No. 5,326,365, is marketed by DePuy Orthopaedics, Inc. under the name Agility™ Ankle. The current surgical technique for the Agility™ Ankle and the associated instrument system for the Agility™ Ankle utilizes a reciprocating or oscillating saw and a freehand method for forming the talar component keel slot.

The utilization of a freehand method is very dependent upon surgeon skill and may provide for lack of accuracy and repeatability in the forming of the slot. For example, the slot may be too deep, too far posterior or too wide for the required geometry of the talar fin. The results of an inaccurate cut include disruption of the anterior and posterior cortex where sufficient bone support occurs. An inaccurate cut may result in the need for excess bone graft to fill the voids from the inaccurate cut. If the slot is cut too deep, talar fractures may occur over time based upon the type of activities of the patient.

It can be seen that an instrumentation system and surgical procedure is needed which is able to increase the precision, accuracy, and repeatability of forming the talar keel slot with the additional benefit of decreased operating room time for the surgeon.

SUMMARY OF THE INVENTION

The present invention is directed to an ankle joint surgical technique and related instrumentation for implanting an ankle joint during ankle replacement surgery. According to the present invention, a specifically designed burr with a round collar and full radius cutting end, may be provided.

Further, a specifically designed burr guide with a posterior hook may be designed to enable the user to locate all implant positional landmarks with respect to the posterior cortex.

Further, after the guide is positioned, the user can burr underneath the tibia by angling his hand and rotating the burr, thereby routing a specific talar implant keel profile track within the radius. This procedure is quick, easy and repeatable, and is done with great precision, plus it does not sacrifice the talar anterior cortex.

The current procedure utilizes a reciprocating saw which is difficult to do, is not repeatable and possibly removes too much bone and sacrifices the talus anterior cortex.

According to one embodiment of the present invention, a kit is provided for preparation of a bone cavity in a bone for implantation of a joint prosthesis. The kit includes a guide defining an opening therethrough. The guide is in cooperation with the prosthesis. The kit also includes a rotatable tool constrainable within the opening of said guide. The tool is adapted for removal of bone to form the bone cavity.

According to another embodiment of the present invention, a guide is provided for guiding a rotatable tool for use in bone preparation of a bone cavity for implantation of a joint prosthesis. The guide is adapted for cooperation with the prosthesis. The guide defines an opening through the guide. The guide constrains the tool within the opening of the guide whereby the tool may be used for removal of bone to form the bone cavity.

According to yet another embodiment of the present invention, a burr tool is provided for use with a guide in joint arthroplasty. The burr tool includes a body, a cutting edge and a stem. A cutting edge extends from the body for cooperation with the guide to assist in positioning the tool with respect to the guide. The stem extends from the body.

According to a further embodiment of the present invention, a method for providing joint arthroplasty is provided, including the steps of resecting a portion of a bone with a tool to form a prosthetic mounting surface, placing a burr guide defining a through opening therein onto the mounting surface of the bone, traversing a rotatable burr tool having a collar longitudinally along the opening to form a slot in the mounting surface of the bone, and inserting a prosthetic component into the slot.

The technical advantage of the present invention includes a subsurface angled ramp and subsurface return arch which cradles and lets the burr rotate out of the burr guide. Another advantage of the present invention is the ability to utilize different burring angle positions to allow the user to burr under the tibia when the tibia and talar are at less than a 900 relative position.

In another aspect of an embodiment of the present invention, a flat bottom trough may be created with the burr and burring guide without the burr being perpendicular to the burring guide.

A further aspect of an embodiment of the present invention is that the anterior cortex of the talus may be preserved utilizing this surgical technique and related instrumentation. The technique leaves the cortices intact providing a sound bone construct for implant stability, and removes the chance of fracturing the anterior cortex.

Another aspect of an embodiment of the present invention is that accurate and repeatable keel slots may be provided without the same degree of experience and skill required for freehand reciprocating saw procedures.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 21 is a perspective view of the talar member of the ankle joint of FIG. 19.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
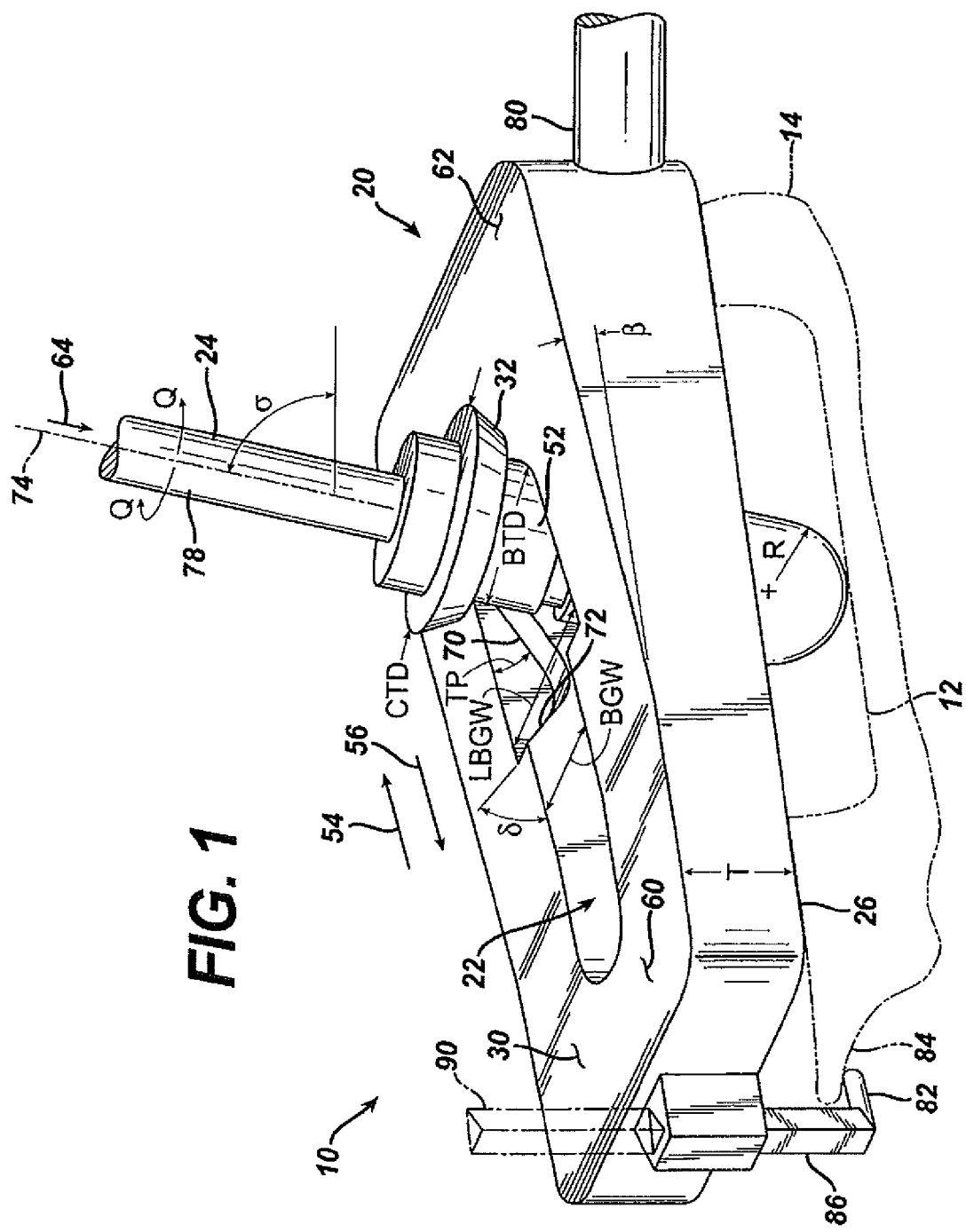
FIG. 1 is a perspective view of a burr and guide in accordance with an embodiment of the present invention.

According to the present invention and referring now to FIG. 1, an embodiment of the present invention is shown as kit 10. Kit 10 is utilized for preparation of bone cavity 12 for implementation of a joint prosthesis (see FIGS. 19-21). The kit 10 includes a guide 20 which defines an opening 22 through the guide 20. The kit 10 further includes a rotatable tool 24 adapted to be constrainable within the opening 22 of the guide 20. The tool 24 is adapted for removal of bone 14 to form the bone cavity 12.

The guide 20 may define a first surface 26 of the guide 20 for cooperation with the bone 14. The guide 20 may also include a second surface 30 which is spaced from and may be parallel to the first surface 26. The tool 24 may include a collar 32 for cooperation with the second surface 30 for assisting in positioning the tool 24.

The kit 10 can, according to the present invention, be utilized to prepare the bone cavity 12 when the room between the talus 14 and the tibia 36 is very limited. For example, and referring now to FIG. 11, the kit 10 is shown positioned between the talus 14 and the tibia 36.

Figure 11:
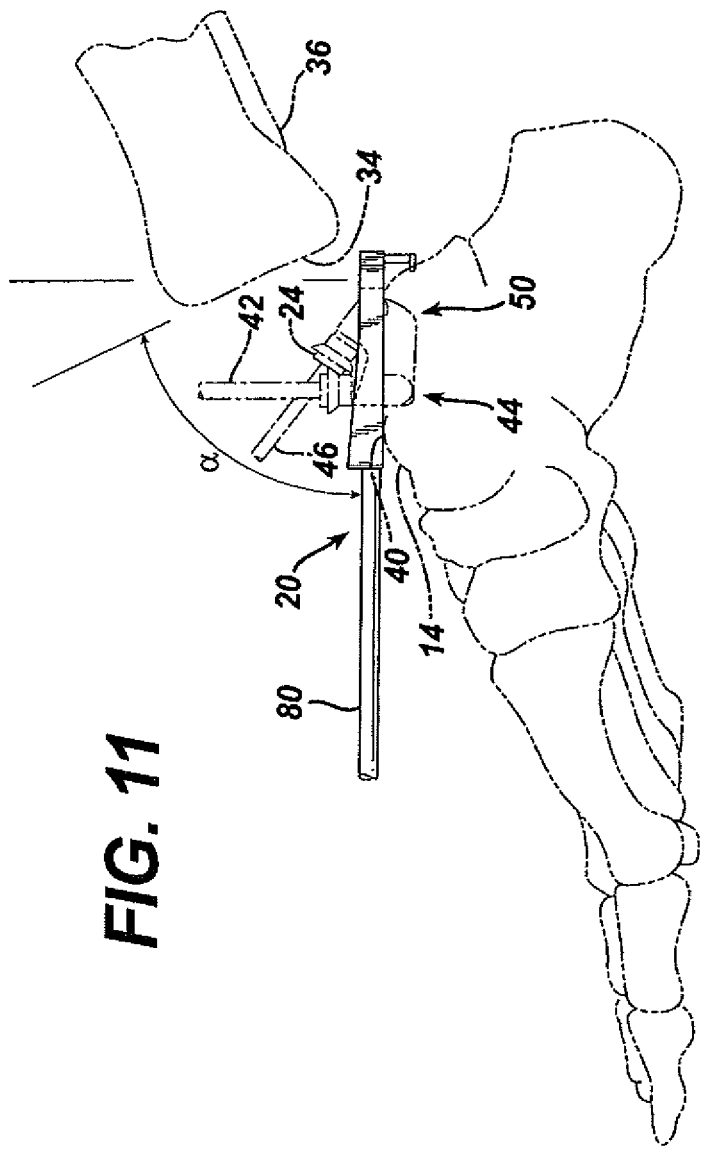
FIG. 11 is a plan view of the burr guide of FIG. 1 in position on a patient's foot.

As shown in FIG. 11, according to an aspect of the present invention, the bone cavity 12 may be prepared where bottom surface 34 of the tibia 36 and top surface 40 of talus 14 are separated by an acute angle α which is less than 90°. The space formed within the acute angle α provides for very limited access to top surface 40 of the talus 14 in order to prepare the bone cavity 12.

To permit the preparation of the bone cavity 12 within such confined space, according to an aspect of the present invention, the burr tool 24 or the burr guide 20 may be adapted to permit the burr tool 24 to be oriented in first direction or position 42 with respect to the burr guide 20 in a first portion 44 of the opening 22 and adapted to be oriented in a second direction or position 46 with respect to the burr guide 20 in a second portion 50 of the opening 22.

By providing the first position 42, as well as a second position 46 for the burr tool 24, the burr tool 24 may be utilized with an angle σ of less than 90°, thereby providing for greater access for the surgeon to the talus 14.

While the opening 22 of the burr guide 20 may have any suitable shape, preferably, and to cooperate with a circular burr tool 24, the opening 22 may have a generally oval shape. Referring again to FIGS. 1 and 11, the positioning of the burr tool 24, with respect to the burr guide 20, may be capable of being positioned in both first position 42 and second position 46 in a number of ways. For example, the opening 22 of the burr guide 20 may have a width BGW which is slightly larger than diameter BTD of burr tool body 52. With such a configuration, the burr tool 24 is free to move about along plane QQ in the direction of arrows 54 and 56. Further, with such a configuration, the burr tool 24 may be rotatable about plane QQ at a variety of angles σ.

The applicants have discovered that by varying the distance from first surface 26 to second surface 30, a desired shape of bone cavity 12 can be provided when confronted with a situation in which the burr tool 24 may need to be placed in positions such as first position 42 and second position 46 to accommodate the limited space between the tibia 34 and the talus 14.

For example, and as shown in FIG. 1, the second surface 30 may include a first portion 60 which is parallel with first surface 26 and a second portion 62 that is skewed from first surface 26. For example, the second portion 62 of second surface 30 may be placed at angle β with respect to first portion 60 of second surface 30. The angular orientation of the second portion 62 of the second surface 30 provides for a burr guide thickness T which may vary along the length of the burr guide 20. It can be readily apparent that by increasing the angle β, the thickness T may be increased further. Also, by varying the angle σ of the tool 24, while varying the angle β of surface 30, a bone cavity 12 may be provided with a large variety of shapes.

As shown in FIG. 1, the collar 32 on the burr tool 24 may be utilized to limit the motion of the tool 24 in the direction of arrow 64. The collar 32 may be utilized to stop the burr tool 24 against second surface 30 or, as shown in FIG. 1, the opening 22 may include a recess portion 66 which has a width LBGW which is wider than the width BGW of the remainder of the opening 22. The width LBGW of the recess 66 may in fact be wider, as shown in FIG. 1, than diameter CTB of the collar 32. The collar 32 thus may move below second surface 30 and seat against subsurface ramp 70. The subsurface ramp 70 may have an angle .pi. and permits the burr tool 24 to move in the direction of arrow 64 further than it would had the collar 32 been stopped by second surface 30. Further, and as shown in FIG. 1, the recess 66 may include a return ramp 72 with a return angle of δ.

While the burr tool 24 may have any suitable shape for rotatively removing material from the talus 14, as shown in FIG. 1, the burr tool 24 may include body 52. The collar 32 extends outwardly along axis 74. Extending diagonally/downwardly from the body 52 along axis 74 is a cutter 76. The cutter 76 may have any suitable shape and may, for example, as shown in FIG. 1, be generally spherical defined by radius R. Extending upwardly from the collar 32 along axis 74 is shaft 78. The shaft 78 may be suitable to secure the burr tool 24 to a power source (not shown).

As shown in FIG. 1, the burr guide 20 may further include a handle 80 extending outwardly from the burr guide 20. The burr guide 20 may also include a positioning feature 82 for cooperation with the talus 14 to properly locate the burr guide 20 with respect to the talus 14. For example, and as shown in FIG. 1, the positioning feature 82 may be in the form of a posterior hook. The posterior hook cooperates with talus posterior cortex 84 of the talus 14.

As shown in FIG. 1, the posterior hook 82 may be retractable and have, for example, a first position 86 which is extended to provide contact between the hook 82 and the talus 14 and a second position 90 as shown in phantom to assist in removal of the burr guide 20 from the talus 14.

Figure 2:
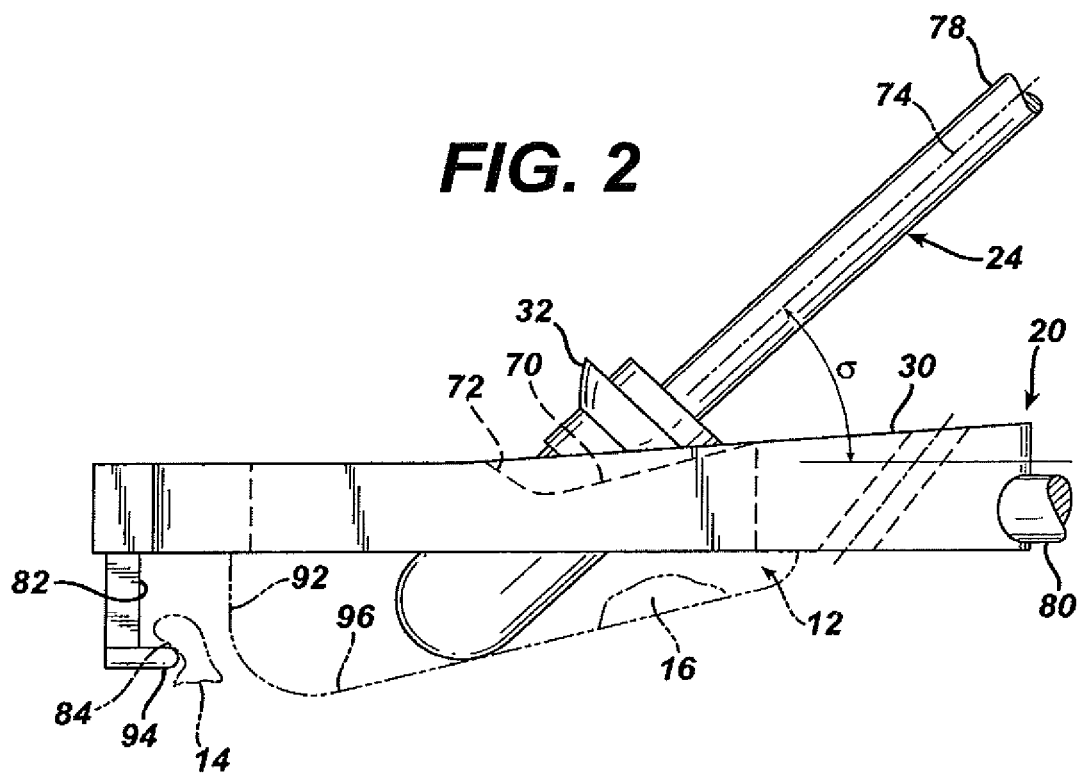
FIG. 2 is a partial plan view of the burr and guide of FIG. 1.

Referring now to FIG. 2, the burr tool 24 is shown with the collar 32 in contact with subsurface ramp 70. As the collar 32 contacts subsurface ramp 70, the cutting surface 76 of the burr tool 24 contacts the talus 14 to form bone cavity 12. As the collar 32 moves first along subsurface ramp 70 and then return ramp 72, the cutting surface 76 moves along the talus 14 forming bone cavity profile 92.

As shown in FIG. 2, the positioning feature or posterior hook 82 may include a protrusion 94 extending from the hook 82 and engaging the talus posterior cortex 84. The bone cavity profile 92 preferably conforms to keel 96 of joint prosthesis 16 (see FIGS. 19, 20, and 21).

Figure 3:
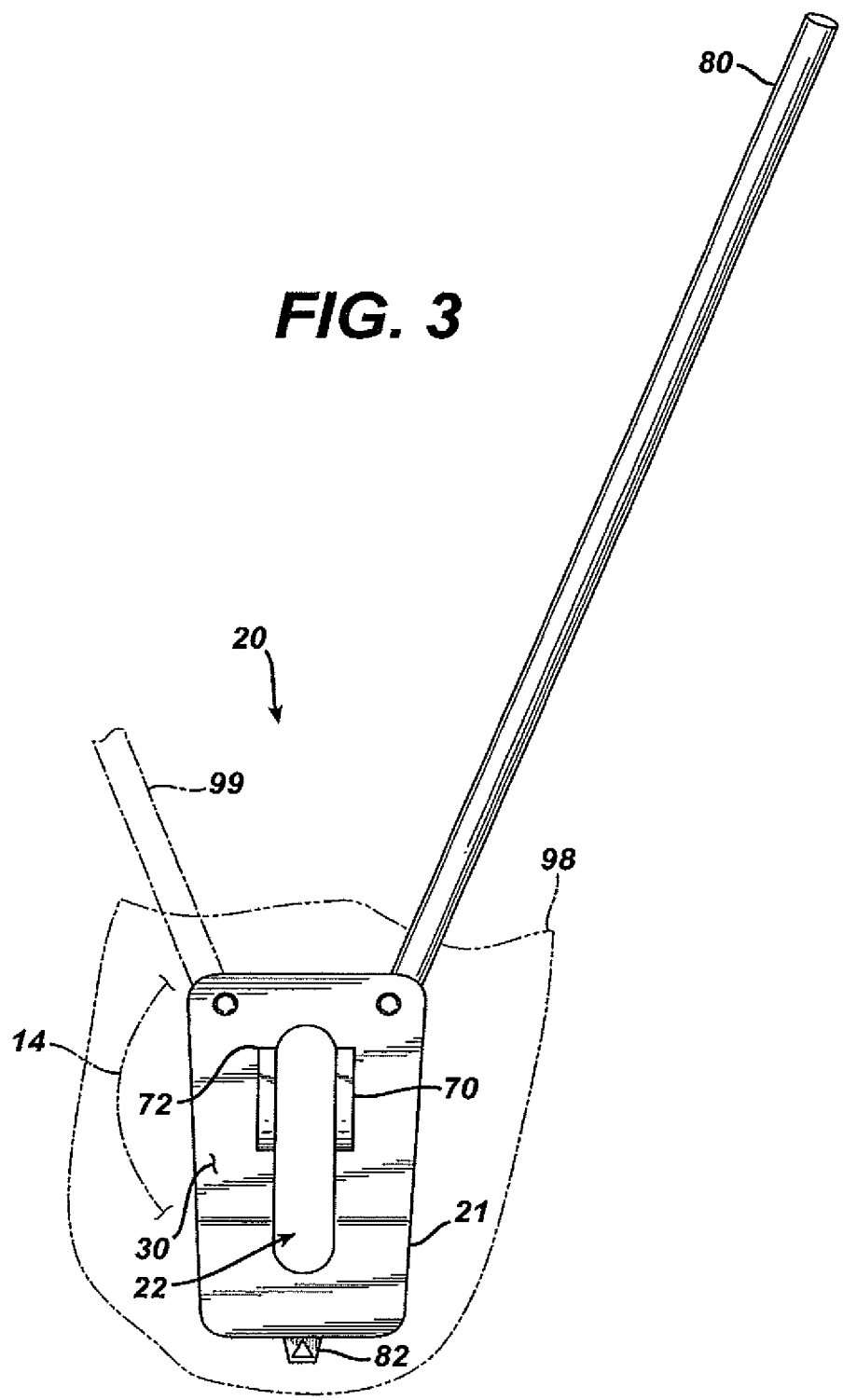
FIG. 3 is a top view of the burr guide of FIG. 1.

Referring now to FIG. 3, the burr guide 20 is shown in position on talus 14 of foot 98. The burr guide 20, as shown in FIG. 3, is for use with left foot 98. A separate burr guide (not shown) may be utilized for right foot (not shown) and may include a handle 99 as shown in phantom.

Figure 4:
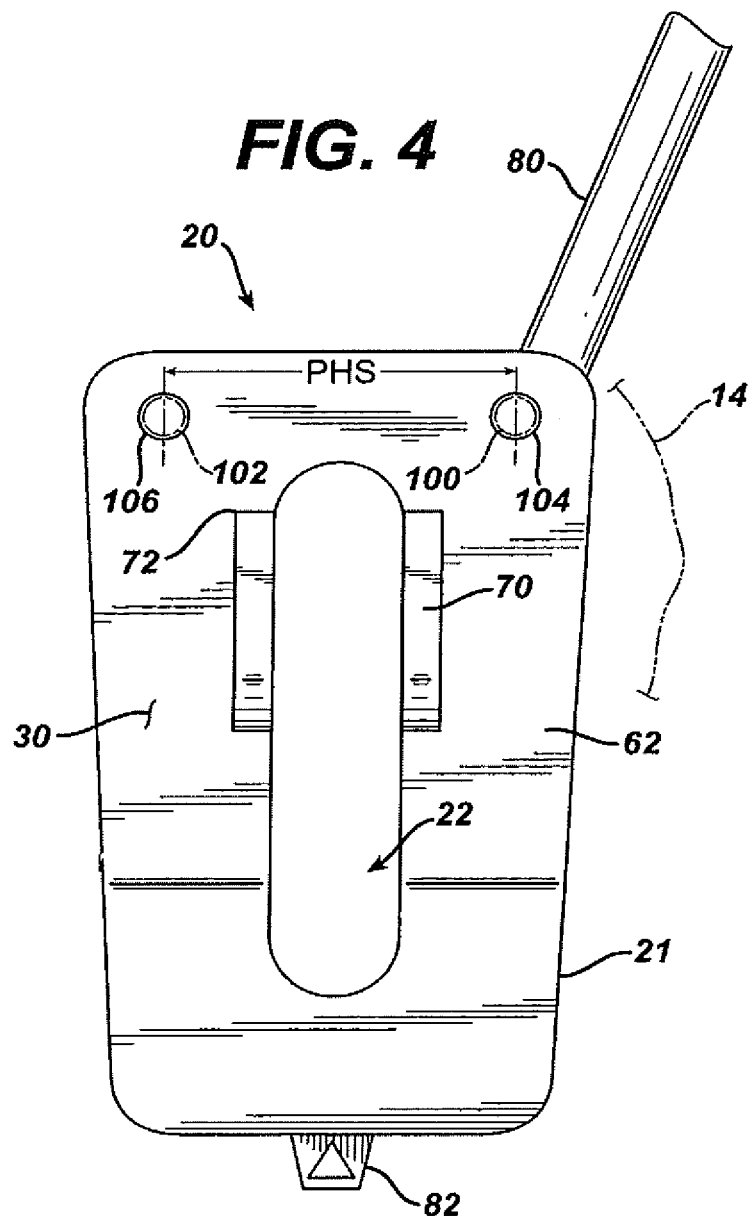
FIG. 4 is a partial top view of the burr guide of FIG. 1.

Referring now to FIG. 4, body 21 of the burr guide 20 is shown in greater detail. The body 21 defines the opening 22 through the body 21. To secure the body 21 against the talus 14, the burr guide 20 may include in addition to hook 82, right and left pins 100 and 102, respectively. The pins 100 and 102 are fitted into right and left pinholes 104 and 106, respectively. The pins 100 and 102 may be self-drilling and tapping pins which are secured to talus 14.

Figure 5:
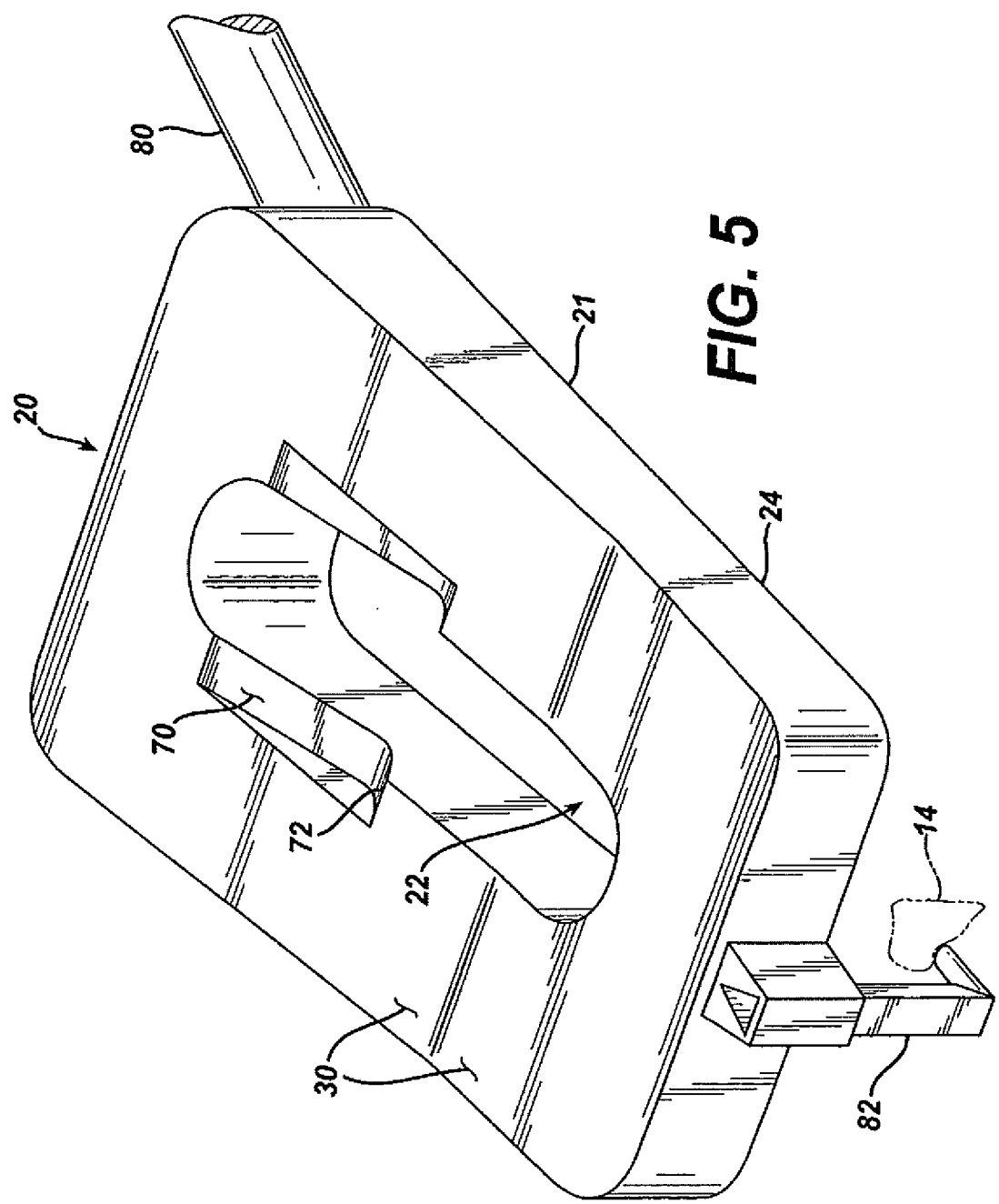
FIG. 5 is a partial perspective view of the burr guide of FIG. 1.

Referring now to FIG. 5, the body 21 of the burr guide 20 is shown in further detail. Referring to FIG. 5, the subsurface ramp 70 and the return ramp 72 are shown recessed from ankle guide top surface 30. The subsurface ramp 70 and return ramp 72 extend outwardly from opening 22 of the body 21.

Figure 6:
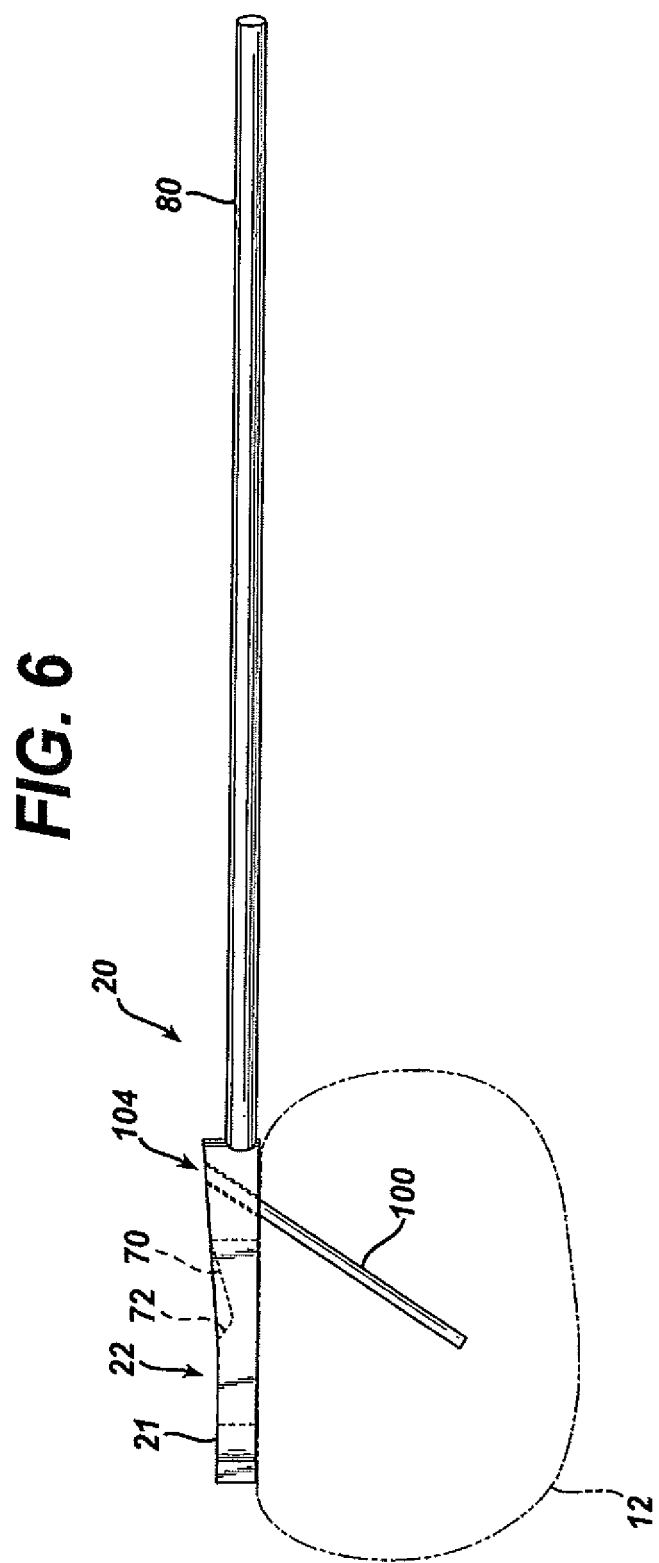
FIG. 6 is a plan view of the burr guide of FIG. 1.

Referring now to FIG. 6, the burr guide 20 is shown with right pin 100 inserted in right pin hole 104. The pins 100 and 102 serve to provide additional stability and support for the burr guide 20 during the forming of the bone cavity 12.

Figure 7:
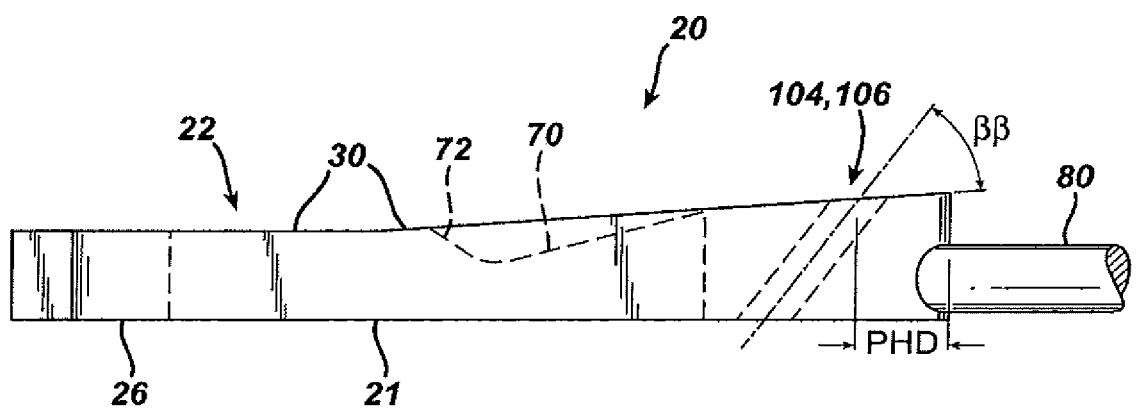
FIG. 7 is a partial plan view of the burr guide of FIG. 1.

Referring now to FIG. 7, the pinholes 104 and 106 are shown in greater detail in body 21. The pinholes 104 and 106 may be spaced in any unique orientation and spacing suitable to assist in the supporting of the burr guide onto the talus. For example, and as shown in FIGS. 4 and 7, the pin holes 104 and 106 may have an angle ββ with respect to top surface 30 of, for example, ββ of approximately 45° and may be spaced a distance PHD of, for example, 0.2 inches from handle end 110 of the body 121. The pinholes 104 and 106 may be spaced apart a distance PDS of, for example, one (1) inch (see FIG. 4).

Figure 8:
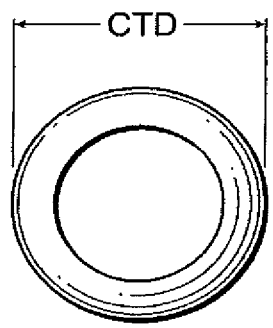
FIG. 8 is a top view of a collar for use with the burr and burr guide of FIG. 1.
Figure 9:
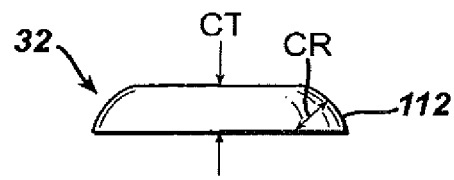
FIG. 9 is a plan view of a collar for use with the burr and burr guide of FIG. 1.

Referring now to FIGS. 8 and 9, the collar 32 is shown in greater detail. The collar 32 may be generally circular and have a collar diameter CDT of, for example, one-half (½) inch. The collar may have a collar thickness CT of, for example, 0.2 inches and a collar radius CR of, for example, 0.2 inches. The collar 32 preferably has an arcuate periphery 112 for cooperation subsurface ramp 70 and return ramp 72 (see FIG. 4).

Referring generally to FIGS. 1 through 9, the burr guide 20 may be made of any suitable, durable material. For example, the burr guide 20 may be made of a metal, for example, a metal which may be sterilized and reutilized in an operating room procedure. For example, the burr guide 20 may be made of cobalt chrome steel, titanium or stainless steel.

The handle 80 may be integral with the body 21 or, for ease of manufacturing and minimizing of cost, the handle 80 may be made of a separate component from the body 21 and either pressed-fit or welded together. Alternatively, the handle 80 may have threadable engagement with the body 21.

Figure 10:
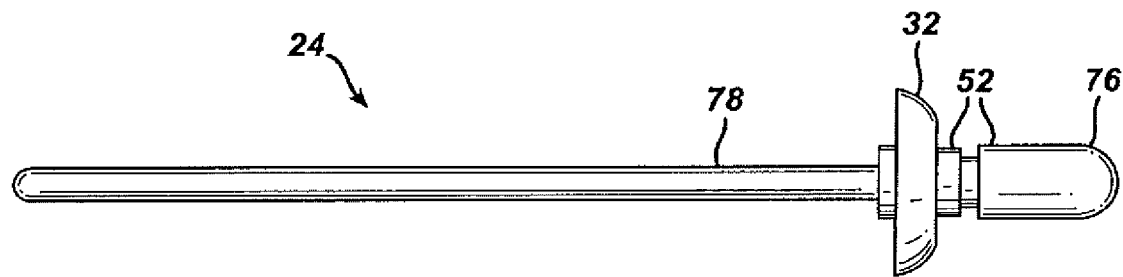
FIG. 10 is a plan view of the burr guide of FIG. 1.

Referring now to FIG. 10, burr tool 24 is shown in greater detail. The burr tool 24 may include body 52 from which collar 32 extends. Extending beyond collar 32 is shank 78. Extending from the opposite end of body 52 is cutter 76. The burr tool 24 may be made of any suitable, durable material and may, for example, be made of stainless steel or cobalt chrome steel. The cutter 76 may be integral to the burr tool body or may be a separate component secured to the body by, for example, braising or welding.

While the kit 10, including the burr guide 20 and the burr tool 24, as shown in FIGS. 1 through 11, is designed and suitable for preparation for the keel of a total ankle prosthesis; it should be appreciated that the kit of the present invention, as well as the burr guide and the burr tool of the present invention, may be utilized to prepare a cavity for installation of a prosthesis at other joints of the human body. One particular well suited joint for use in this invention is the preparation of a unicondyle knee, femoral or tibial component.

Figure 12:
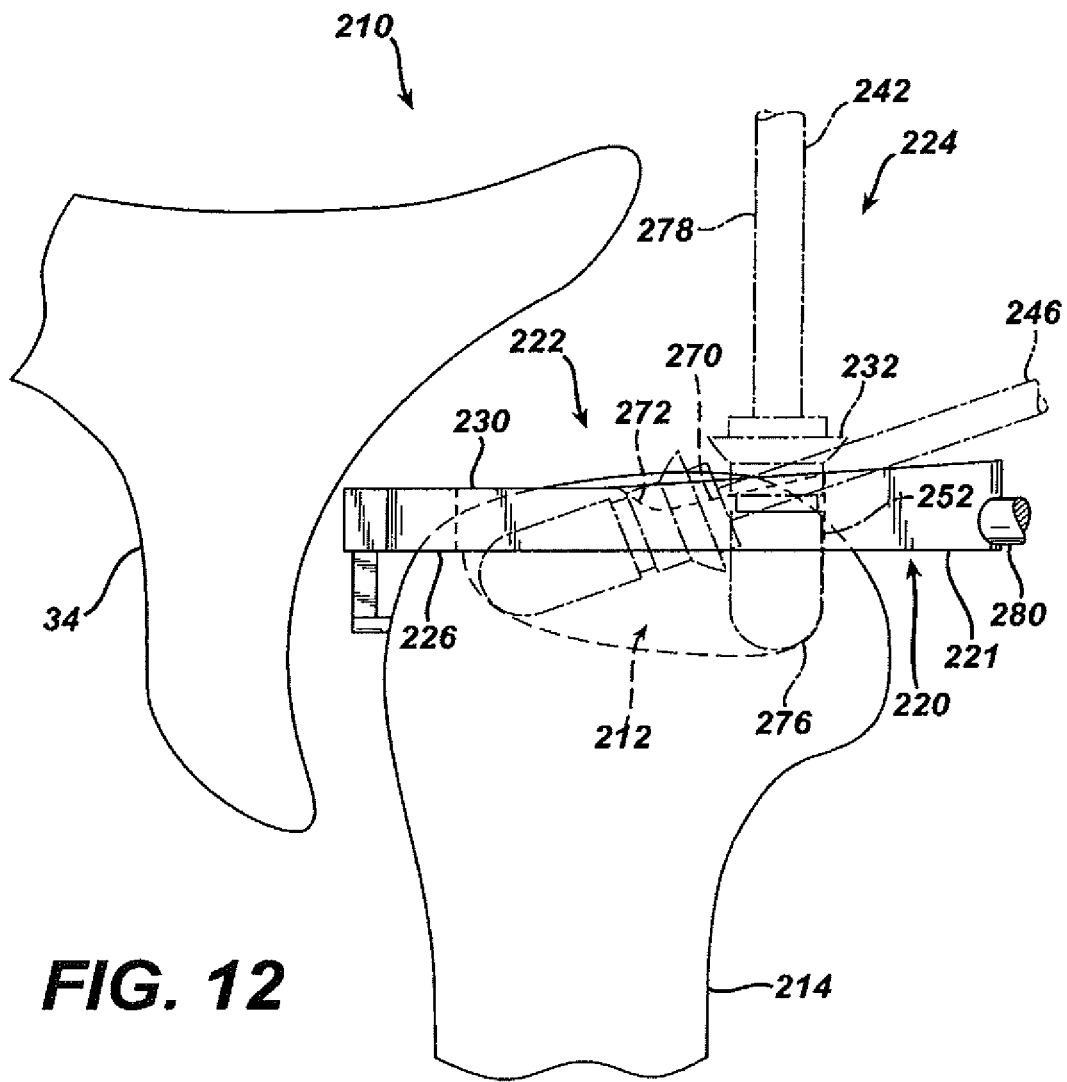
FIG. 12 is a plan view of burr guide of FIG. 1 for use in partial knee arthroplasty with the guide in position on a patient's knee.

For example, and as shown in FIG. 12, kit 210 may be utilized to prepare cavity 212 in femur 214. Kit 210 may be similar to kit 10 of FIGS. 1 through 11 but may be adapted to form the cavity 212 for the femur 214. Like kit 10 of FIGS. 1 through 11, kit 210 of FIG. 12 permits the forming of cavity 212 where the bones in this case, tibia 34 and femur 214, provide for only limited access to the cavity 212.

The kit 210 includes a burr tool 224 similar to the burr tool 24 of the kit 10 of FIGS. 1 through 11, as well as burr guide 220, which is similar to burr guide 20 of the kit 10 of FIGS. 1 through 11.

The burr guide 220 includes a body 221 from which handle 280 extends. The body 221 defines opening 222 there through. The burr tool 224 matingly fits within opening 222. The burr guide 220 includes a first surface 226 which is in contact with the femur 214 as well as an angled top surface 230 into which are formed subsurface ramp 270 and return ramp 272. The burr tool 224 includes a first position 242 and a second position 246 which is skewed and spaced from the first position 242. The burr tool 224 is permitted to move from first position 242 through second position 246 to form the cavity 212 in the femur 214.

The burr tool 224, similar to the burr tool 24 of the kit 10 of FIGS. 1 through 11, includes body 221. A cutting tip 276 extends outwardly from the body 221. Also extending from body 221 is a rounded collar 232. A shank 278 extends outwardly from rounded collar 232. While the kit 210, as shown in FIG. 12, is shown for use in preparing one of two uni-condyle cavities 212, it should be appreciated that the kit 210 may equally work to form the other cavity for the preparation of a medial condyle as well as for a lateral condyle. Further, it should be appreciated that the kit 210 or a similar kit, may be utilized to prepare cavities for uni-condyle knee portions for the tibia 34 as well.

Referring now to FIGS. 13 through 18, kit 310 is shown for preparing a bone cavity 376 for talus 314. Kit 310 is similar to kit 10 of FIGS. 1 through 11 except that kit 310 includes burr tool guide 320 and burr tool 324 adapted such that the axis 374 of the burr tool 324, when utilized with the burr tool guide 320, provides for the burr tool 324 to move first along axis 374 until the burr tool 324 is fully seated against the burr tool guide 320 and then to move along an axis parallel to the axis 374 and to then be removed from the burr tool guide along axis 374. The kit 310 provides for a simpler burr tool guide 320 where there is ample room for the introduction of the burr tool 324 between the talus 314 and the tibia.

Figure 13:
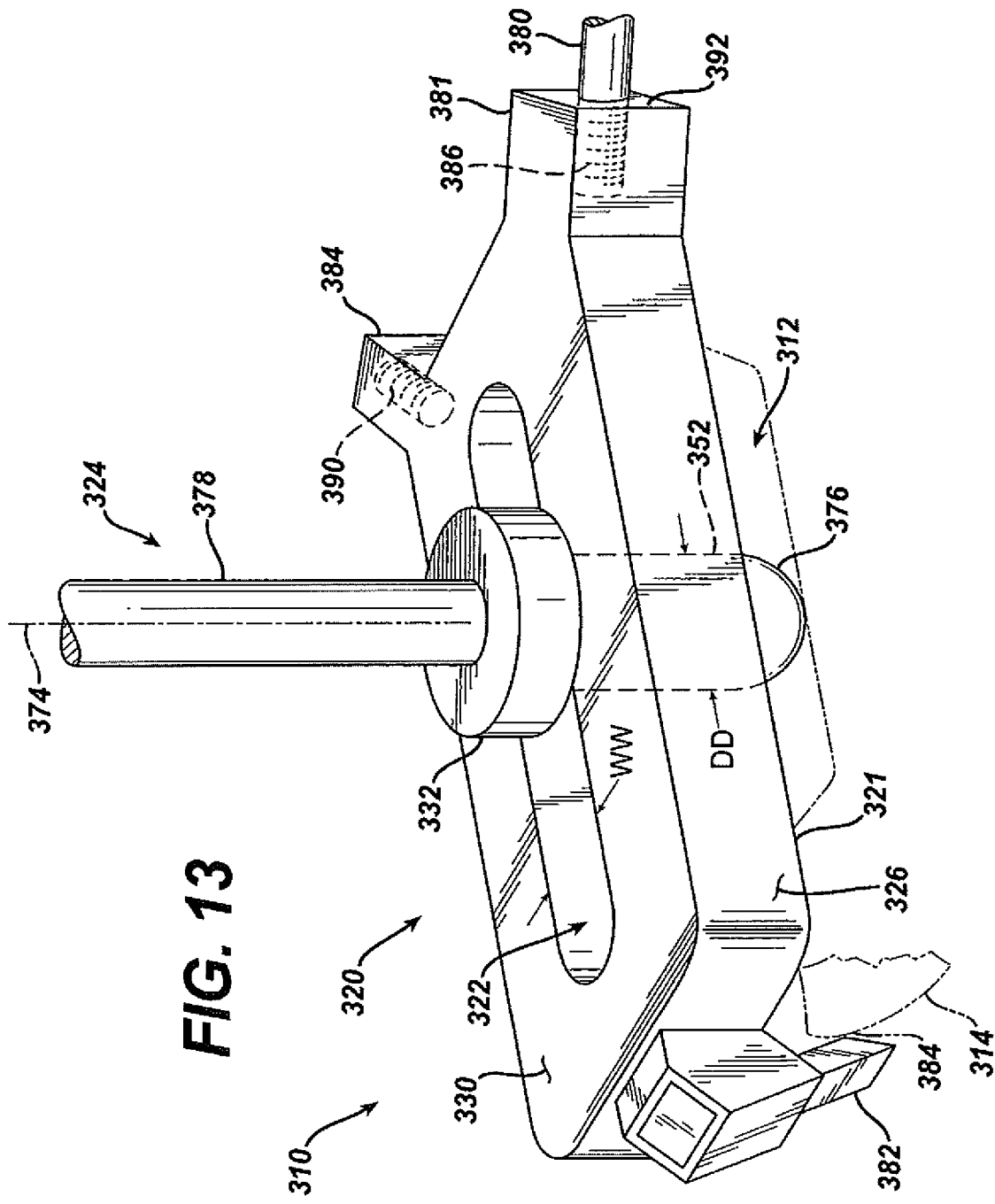
FIG. 13 is a partial perspective view of another embodiment of the kit, burr and burr guide of the present invention.

Referring to FIG. 13, the burr tool 324 includes a body 352 and a cutting tip 376 which extends from the body 352. A collar 332 extends from the body 352 in a direction opposed to the cutting tip 376. A shank 378 extends outwardly from collar 332.

The burr tool guide 320 includes a body 321 which defines an opening or slot 322. To provide for a well defined bone cavity 312, the body 352 of the burr tool 324 may have a cylindrical shape with a diameter DD which is slightly smaller and may even be matingly fitted with width WW of the slot opening 322 of the body 321 of the burr tool guide 320.

As shown in FIG. 13, bottom surface 326 and top surface 330 of the body 352 of the burr tool guide 320, unlike the burr tool guide 20 of FIGS. 1 through 11, are each planar and they are parallel to each other. The burr tool guide 320, similar to the burr tool guide 20 of FIGS. 1 through 11, includes a posterior hook 382. Posterior hook 382 of the burr tool guide 320 is similar to the hook 82 of the guide 20 and matingly contacts cortex 384 of the talus 314. To avoid the need for both right-hand and left-hand burr tool guides, the burr tool guide 320 of FIG. 13 may include a first handle position 38 and a second handle position 384 extending from the body 352 of the burr tool guide 320. The first and second handle position 382 and 384 may include internal threads 386 and 390 which mate with external threads 392 on burr tool guide handle 380.

Figure 14:
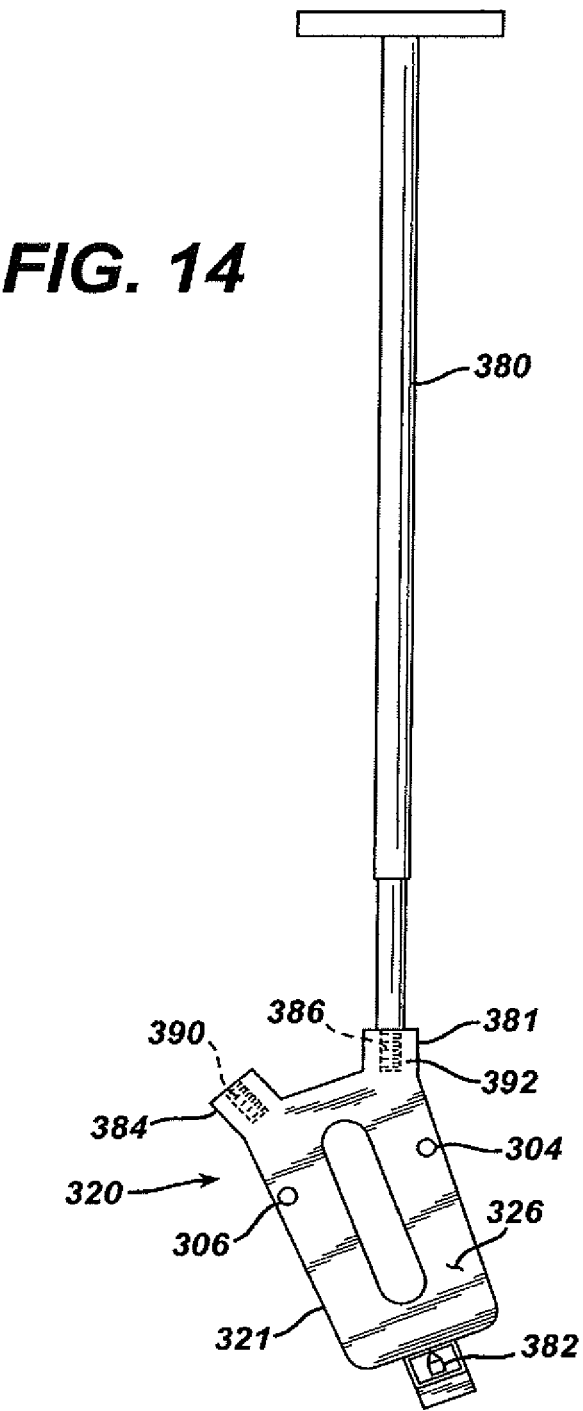
FIG. 14 is a bottom view of the burr guide of FIG. 13.

Referring now to FIG. 14, the burr tool guide 320 is shown in greater detail. The burr tool guide 320 includes body 321 as well as burr tool guide handle 380. The burr tool guide 320 includes posterior hook 382 which extends outwardly from bottom surface 326 of the burr tool guide 320. The burr tool guide 320 preferably includes pinholes 304 and 306 for cooperation with pins (not shown) for securing the burr tool guide 320 to the talus 314.

Figure 15:
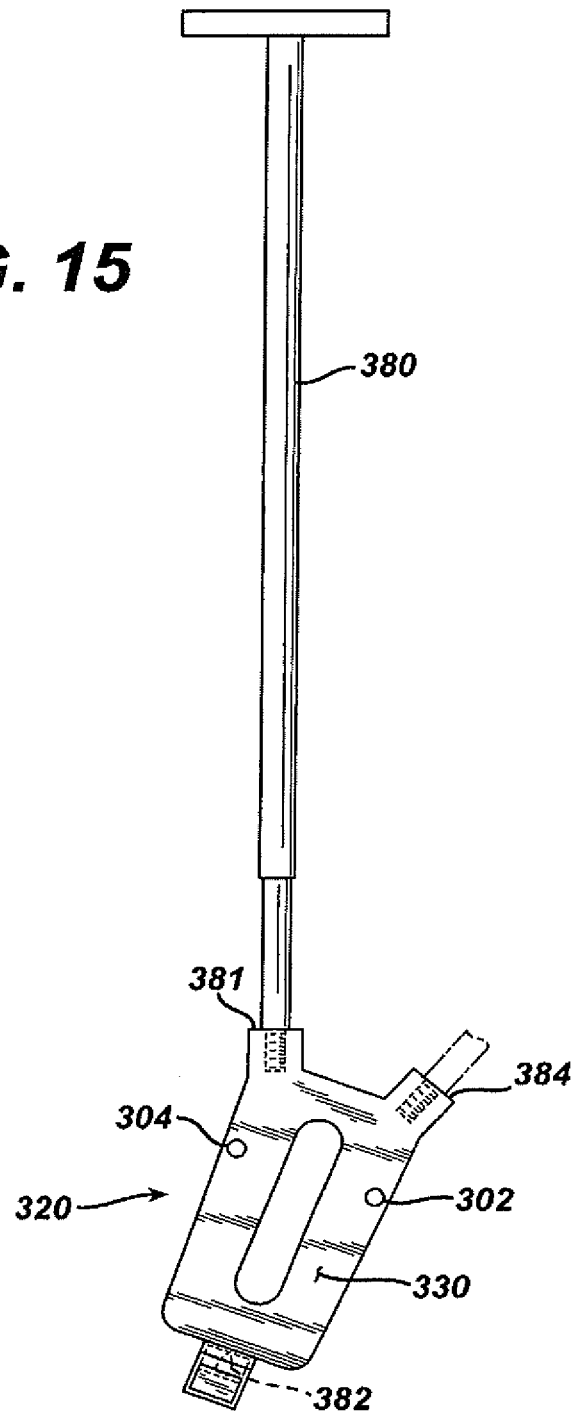
FIG. 15 is a top view of the burr guide of FIG. 13.

Referring now to FIG. 15, the burr tool guide 320 is shown with top surface 330 exposed. Referring to FIG. 15, the handle 380 is shown in solid in first handle position 381 and in phantom in second handle position 384.

Figure 16:
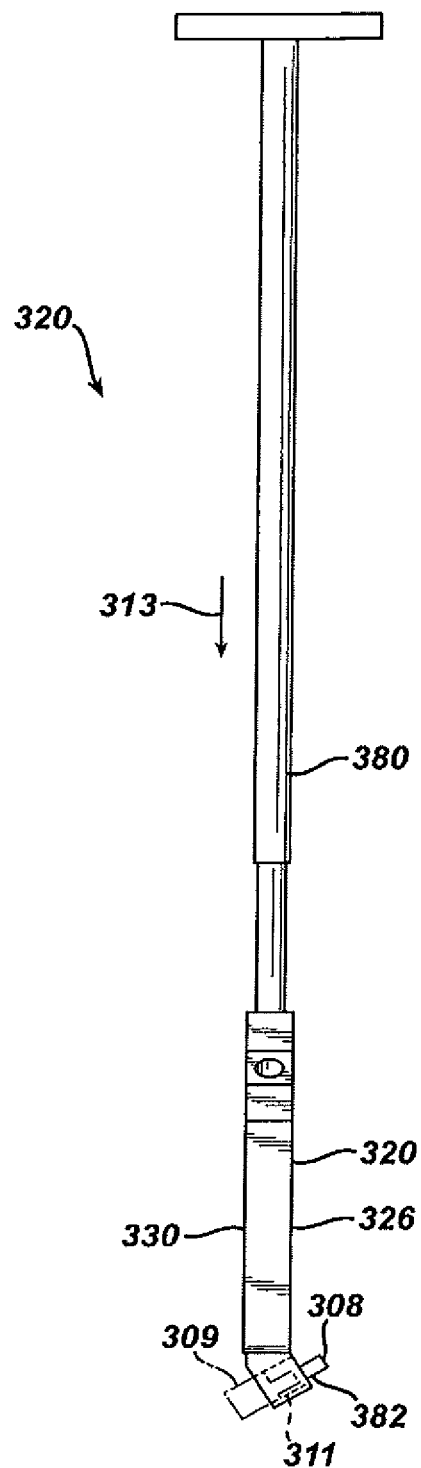
FIG. 16 is a plan view of the burr guide of FIG. 13.

Referring now to FIG. 16, the burr tool guide 320 is shown with the posterior hook 382 in a first position 308 as shown in solid, and in a second retracted position 309 as shown in phantom. By providing the hook 382 which may be slidably fit within hook body 311, the burr tool guide may be more easily slid into position along the direction of arrows 313 when the hook 382 is in the retracted second position 309 as shown in phantom.

Figure 17:
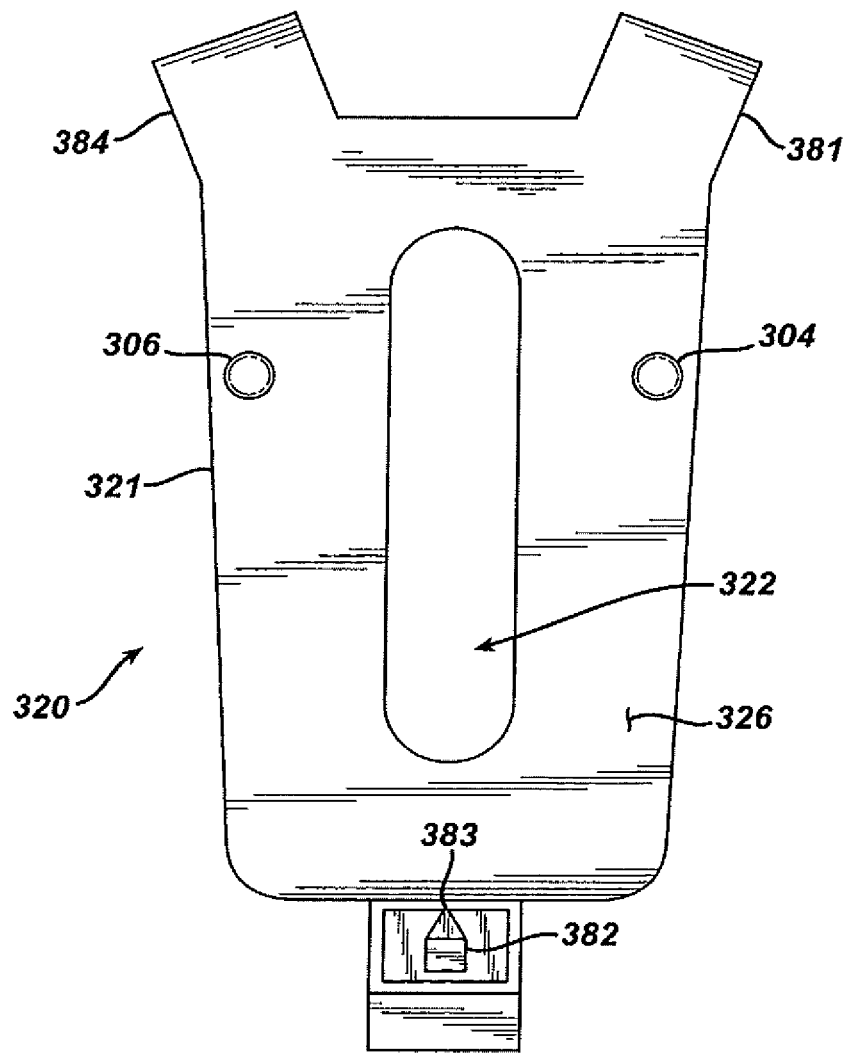
FIG. 17 is a partial bottom view of the burr guide of FIG. 13.

Referring now to FIG. 17, the body 321 of the burr tool guide 320 is shown in greater detail. The posterior hook 382 is shown in greater detail. The posterior hook 382 may, for example as shown in FIG. 17, have a generally v-shape with an outer point or protrusion 383 which provides for secure penetration into the talus 314.

Figure 18:
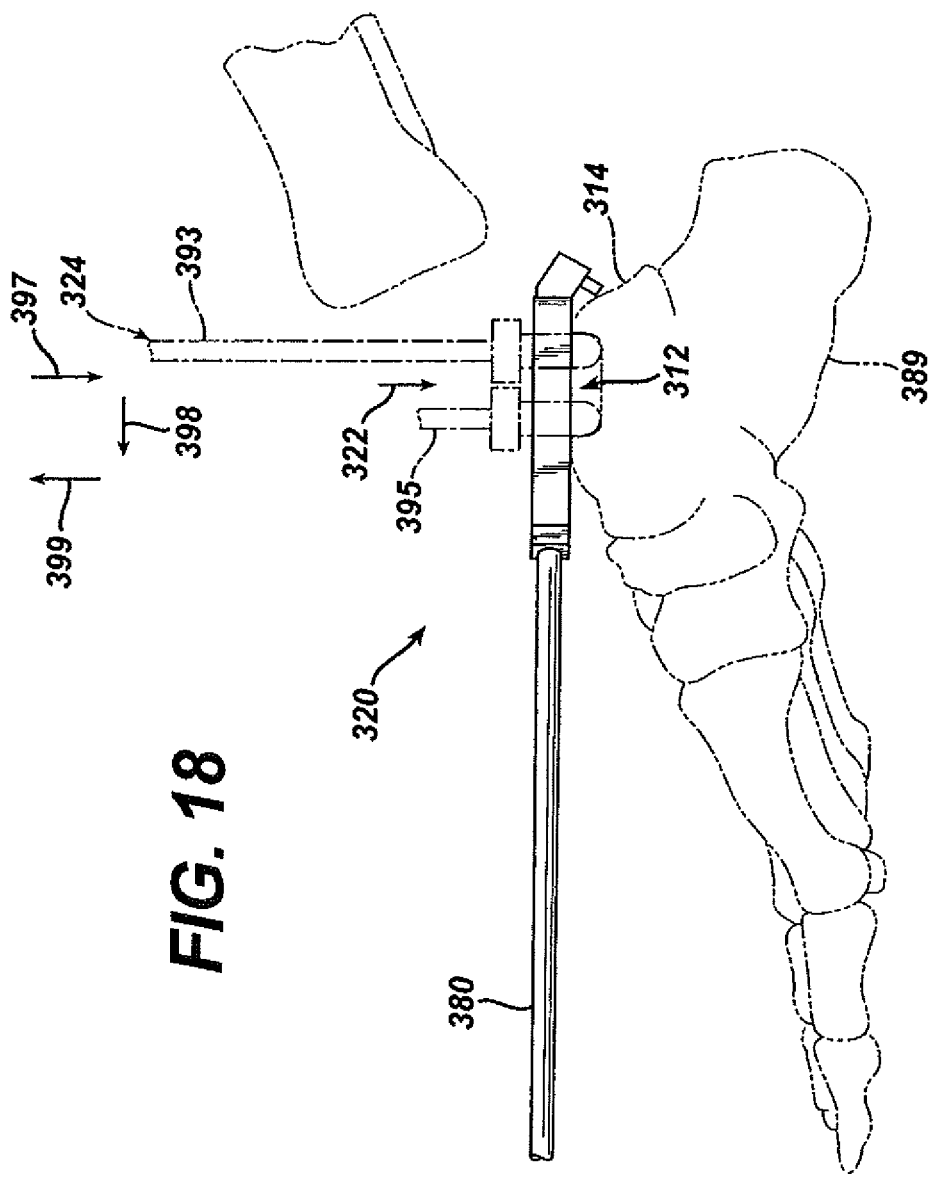
FIG. 18 is a plan view of the burr guide of FIG. 13 in position on a patient's foot.

Referring now to FIG. 18, the burr tool guide 320 is shown in position against the talus 314 of foot 389. The burr tool 324 is utilized to form bone cavity 312. The burr tool 324 is shown in solid in first position 393 and in phantom in second position 395. The burr tool 392 moves within the opening 322 of the burr tool guide moving first in direction of arrow 397 until the burr tool 324 is into first position as shown in solid 393. The burr tool 324 then moves in the direction of arrow 398 until the burr tool 324 is in second position 395 as shown in phantom. The burr tool 324 then moves in direction of arrow 399 until it is separated from the burr tool guide 322. Thus, the burr tool 324 forms the bone cavity 312.

Figure 19:
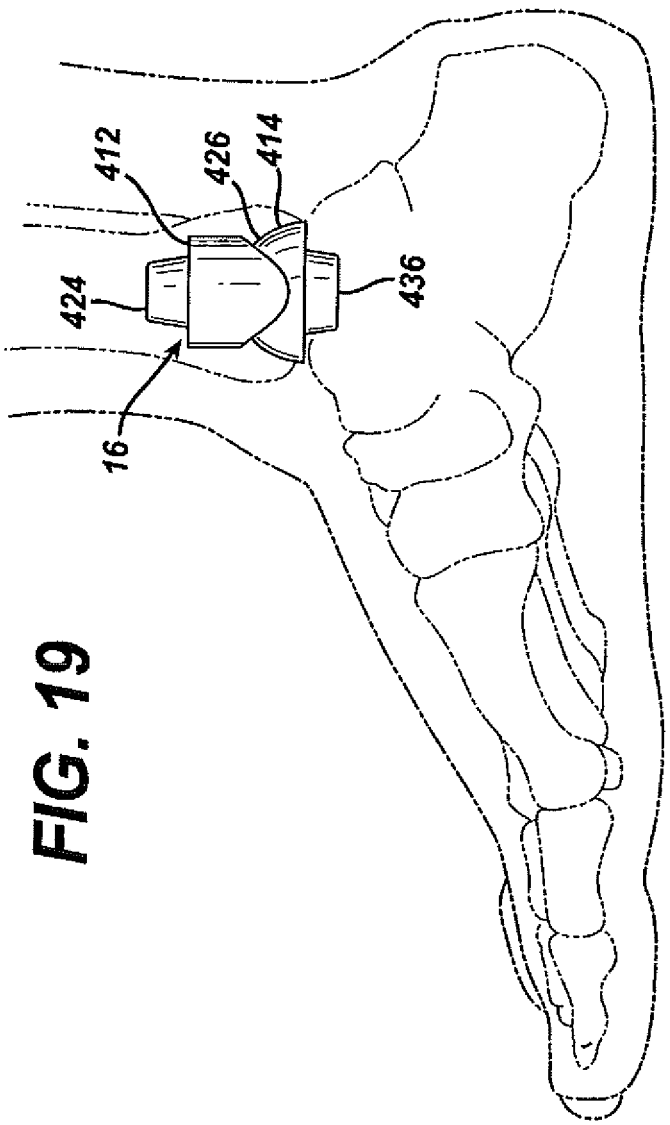
FIG. 19 is a side elevational view of an ankle joint which may be implanted utilizing either the burr guide of FIG. 1 or that of FIG. 13.
Figure 20:
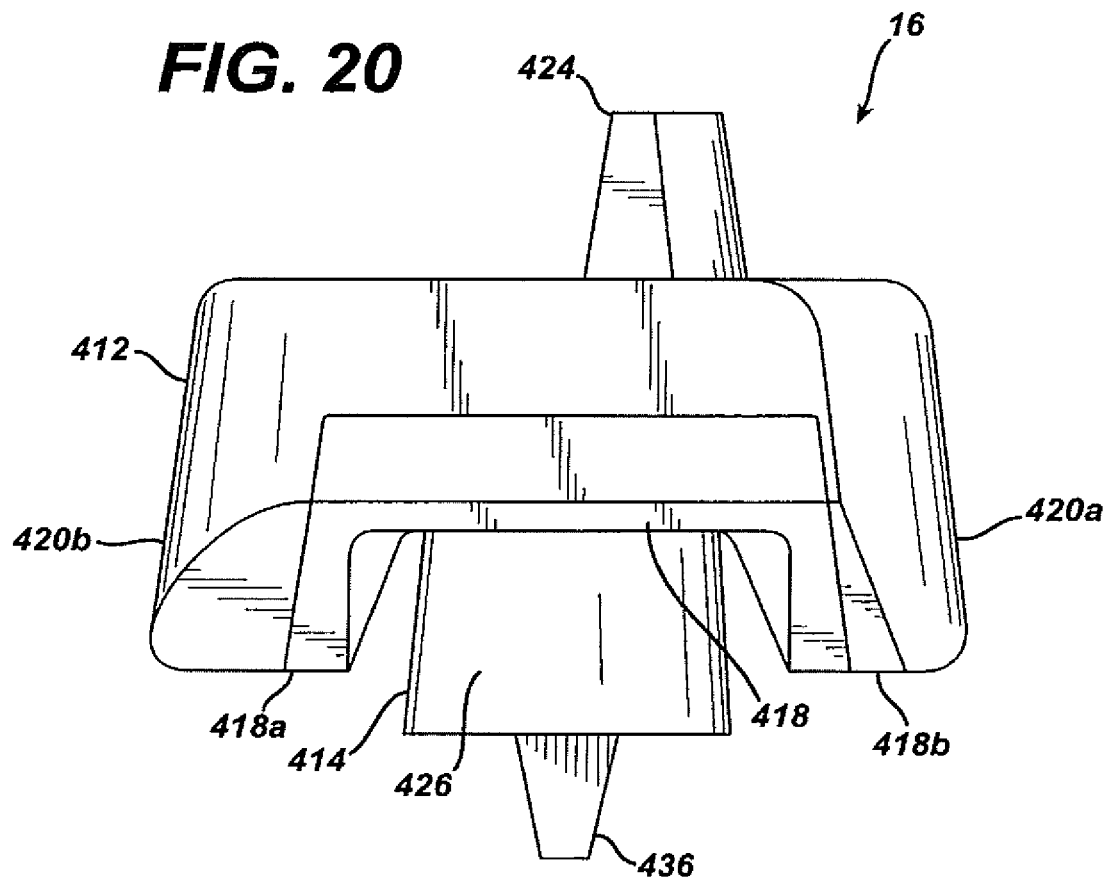
FIG. 20 is a rear elevational view of the ankle joint of FIG. 19.

Referring now to FIGS. 19 through 21, joint prosthesis 16 is shown in greater detail. While it should be appreciated that the kit, burr tool and burr tool guide of the present invention may be utilized to provide a bone cavity for any total arthroplasty joint, it should be appreciated that the invention is well suited to provide for ankle joint prosthesis 16. Joint prosthesis 16 is more fully described in U.S. Pat. No. 5,326,365 to Alvine incorporated herein in its entirety by reference.

Referring to FIGS. 19 through 21, the implantable ankle device 16 is shown. The joint prosthesis 16 is configured for replacement surgery wherein the patient's ankle is replaced. The ankle device 16 has a tibial member 416 and a talar member 414 which interacts to provide flexion and tension similar to that of a normal ankle. The implanted ankle 16 has a compact shape which requires minimum removal of the patient's bone and tissue.

Referring to FIG. 20, tapering dome portion 426 of the talar member 414 fits in a complimentary manner with tibial bearing 418. The concave surface of the tibial bearing 418 fits against the dome portion 426. Side portions 418a and 418b of the tibia bearing proximate the positioning walls 420a & 420b and gate the sides of the dome portion 426. The dome portion 426 slides and pivots relative to the tibial bearing 418.

Referring now to FIG. 21, the dome portion 426 widens slightly from the anterior to posterior. The distance between the side portions 418a and 418b also widen in a similar manner, which keeps the members 412 and 414 aligned, but also provides clearance between sides of the dome portion 426 and the side portions 418a and 418b to allow turning of the joint to either side while restricting the lateral rotation with any range comparable to that of a natural ankle joint. A strut 424 extends upwardly from the tibial base plate 22 opposite the tibial bearing 18.

The strut 424 is secured to the tibia.

A talar strut 436 extends downward into the talus to keep talar member 414 properly aligned when implanted.

By providing a burr tool with rounded shoulder stop collar, a profile may be obtained with a continually angularly rotating position of the burr tool during the cut.

By providing a burr tool guide with an outer-profile shape like the implant, an accurate repeatable and simple cut can be performed on the bone.

By providing a hook on the bone, as well as locating holes, an accurate position of the guide may be provided.

By providing subsurface angular burr ramp, as well as a subsurface return arch, the burr tool may be cradled and the burr tool may be permitted to come in and rotate out with any burr tool in a variety of angular positions to permit the removal of the bone cavity in areas in which the access to the joint is limited.

By providing different burring angular positions, a burr tool may be utilized under or between adjoining bones of a joint.

By providing subsurface angles and returns arches, a flat-bottomed trough may be provided without the burr being perpendicular during the cut.

By providing a burr guide to limit the removal of material from the talus, the anterior cortex of the talus may be maintained. By providing the cortex's intact, a sound bone construct can be provided for implant stability and the removal of the chances of fracturing the anterior cortex.

By replacing a free-handed reciprocal saw procedure with a rotating burr tool, confined within a burr tool guide, the quality and consistency of the bone cavity may be optimized.

Although the present invention and its advantages have been described in detail, it should be understood that various changes, substitutions, and alterations can be made therein without departing from the spirit and scope of the present invention as defined by the appended claims.

What is claimed is:

1. A method involving (i) a cutting guide having a tibia-facing top surface that defines a tibia-facing top opening, a talus-facing bottom surface that defines a talus-facing bottom opening, and a tool passage extending between the tibia-facing top opening and the talus-facing bottom opening, and (ii) a tool having a distal portion that includes a cutting member and a stop collar, comprising:
   resecting bone of a talus to form a talus mounting surface;
   locating the cutting guide between the talus and a tibia so that the talus-facing bottom surface is positioned on the talus mounting surface; and
   forming a keel cavity in the talus while the cutting guide is located between the talus and the tibia on the talus mounting surface including (i) advancing the cutting member through the tool passage and into contact with the talus while the talus-facing bottom surface is positioned on the talus mounting surface, and (ii) manipulating the tool within the tool passage while the stop collar is in contact with the cutting guide.

2. The method of claim 1, wherein:
   the cutting guide further has a ramp surface located within the tool passage,
   the locating step further includes locating the cutting guide between the talus and the tibia so that the ramp surface faces the tibia while the talus-facing bottom surface is positioned on the talus mounting surface, and
   the forming step further includes manipulating the tool within the tool passage while (i) the stop collar is in contact with the ramp surface, and (ii) the ramp surface faces the tibia.

3. The method of claim 2, wherein:
   the ramp surface includes a first ramp surface portion and a second ramp surface portion,
   the tibia-facing top surface extends in a direction,
   the first ramp surface portion slopes downwardly in relation to the direction, and
   the second ramp surface slopes upwardly in relation to the direction.

4. The method of claim 3, wherein the forming step further includes:
   advancing the tool within the tool passage while the stop collar is in contact with the first ramp surface portion, and thereafter
   advancing the tool within the tool passage while the stop collar is in contact with the second ramp surface portion.

5. The method of claim 1, further comprising:
   implanting a talus component of an ankle prosthesis system in the talus, wherein (i) the talus component has a keel, and (ii) the implanting step includes implanting the talus component in the talus so that the keel is located in the keel cavity.

6. The method of claim 1, wherein:
   the cutting guide further has a hook positioning structure, and
   the locating step further includes catching a posterior cortex portion of the talus with the hook positioning structure while the talus-facing bottom surface is positioned on the talus mounting surface.

7. The method of claim 6, wherein:
   the cutting guide further has a main body that defines the tool passage; and
   the hook positioning structure is adjustably mounted to the main body.

8. The method of claim 1, wherein:
   the forming step further includes (i) positioning the tool within the tool passage so that the tool forms a first angle with respect to the tibia-facing top surface, and (ii) further positioning the tool within the tool passage so that the tool forms a second angle with respect to the tibia-facing top surface, and the first angle is different from the second angle.

9. The method of claim 1, wherein the manipulating step is performed while (i) the stop collar extends through the tibia-facing top opening, and (ii) the cutting member extends through the talus-facing bottom opening.

10. The method of claim 9, wherein the manipulating step is further performed while the cutting member also extends through the tibia-facing top opening.

11. The method of claim 1, wherein the manipulating step is performed while the stop collar is spaced apart from the talus-facing bottom opening.

12. A method involving (i) a cutting guide having a tibia-facing top surface that defines a tibia-facing top opening, a talus-facing bottom surface that defines a talus-facing bottom opening, and a tool passage extending between the tibia-facing top opening and the talus-facing bottom opening, and (ii) a tool having a distal portion that includes a cutting member and a stop collar, comprising:

resecting bone of a talus to form (i) a bone space previously occupied by talus bone, the bone space being located between the talus and a tibia, and (ii) a talus mounting surface;

locating the cutting guide in the bone space so that the talus-facing bottom surface is positioned on the talus mounting surface; and forming a keel cavity in the talus while the cutting guide is located in the bone space and on the talus mounting surface, the forming step including (i) advancing the cutting member through the tool passage and into contact with the talus while the talus-facing bottom surface is positioned on the talus mounting surface, and (ii) manipulating the tool within the tool passage while the stop collar is in contact with the cutting guide.

13. The method of claim 12, wherein:

the cutting guide further has a ramp surface located within the tool passage, the locating step further includes locating the cutting guide between the talus and the tibia so that the ramp surface faces the tibia while the talus-facing bottom surface is positioned on the talus mounting surface, and the forming step further includes manipulating the tool within the tool passage while (i) the stop collar is in contact with the ramp surface, and (ii) the ramp surface faces the tibia.

14. The method of claim 13, wherein:

the ramp surface includes a first ramp surface portion and a second ramp surface portion, the tibia-facing top surface extends in a direction, the first ramp surface portion slopes downwardly in relation to the direction, and the second ramp surface slopes upwardly in relation to the direction.

15. The method of claim 14, wherein the forming step further includes:

advancing the tool within the tool passage while the stop collar is in contact with the first ramp surface portion, and thereafter advancing the tool within the tool passage while the stop collar is in contact with the second ramp surface portion.

16. The method of claim 12, further comprising:

implanting a talus component of an ankle prosthesis system in the talus, wherein (i) the talus component has a keel, and (ii) the implanting step includes implanting the talus component in the talus so that the keel is located in the keel cavity.

17. The method of claim 12, wherein:

the cutting guide further has a hook positioning structure, and the locating step further includes catching a posterior cortex portion of the talus with the hook positioning structure while the talus-facing bottom surface is positioned on the talus mounting surface.

18. The method of claim 17, wherein:

the cutting guide further has a main body that defines the tool passage; and the hook positioning structure is adjustably mounted to the main body.

19. The method of claim 12, wherein:

the forming step further includes (i) positioning the tool within the tool passage so that the tool forms a first angle with respect to the tibia-facing top surface, and (ii) further positioning the tool within the tool passage so that the tool forms a second angle with respect to the tibia-facing top surface, and the first angle is different from the second angle.

20. The method of claim 12, wherein the manipulating step is performed while (i) the stop collar extends through the tibia-facing top opening, and (ii) the cutting member extends through the talus-facing bottom opening.

21. The method of claim 20, wherein the manipulating step is further performed while the cutting member also extends through the tibia-facing top opening.

22. The method of claim 12, wherein the manipulating step is performed while the stop collar is spaced apart from the talus-facing bottom opening.

* * * * *